(12) United States Patent
Yang et al.

(10) Patent No.: US 6,512,982 B2
(45) Date of Patent: Jan. 28, 2003

(54) METHODS AND SYSTEMS FOR EVALUATING DEFECTS IN METALS

(75) Inventors: Ling Yang, Clifton Park, NY (US); Robert Falsetti, Schenectady, NY (US)

(73) Assignee: General Electric Company, Schenectady, NY (US)

(*) Notice: Subject to any disclaimer, the term of this patent is extended or adjusted under 35 U.S.C. 154(b) by 123 days.

(21) Appl. No.: 09/742,667

(22) Filed: Dec. 20, 2000

(65) Prior Publication Data

US 2002/0111749 A1 Aug. 15, 2002

(51) Int. Cl.[7] .................. G01N 31/20; G01N 33/20; G21C 17/00
(52) U.S. Cl. .............. 702/34; 702/36; 700/30; 707/102
(58) Field of Search ................ 702/34, 36, 1, 702/108; 700/30, 31, 106; 707/102, 103; 73/579, 587, 602

(56) References Cited

U.S. PATENT DOCUMENTS

| | | |
|---|---|---|
| 4,908,775 A | 3/1990 | Palusamy et al. |
| 4,947,341 A | 8/1990 | Shine |
| 5,140,528 A | 8/1992 | Swaminathan et al. |
| 5,715,180 A | 2/1998 | Hu |
| 5,717,607 A | 2/1998 | Hu |
| 5,768,129 A | 6/1998 | Miyamoto |
| 5,878,433 A | 3/1999 | Miyamoto |
| 6,199,431 B1 | 3/2001 | Nath et al. |

FOREIGN PATENT DOCUMENTS

EP    1094127    *  4/2001

* cited by examiner

Primary Examiner—Kamini Shah
(74) Attorney, Agent, or Firm—Perkins Coie LLP

(57) ABSTRACT

A method and system for evaluating structural defects in metals is provided. In one embodiment, the method recognizes that the acceptability of a given defect is principally determined by the four basic parameters of operating temperature, operating stress, defect area, and defect shape. Ranges are established for each of these four basic parameters, and intermediate values within these ranges are selected to create a series of index value data sets. The method evaluates these index value data sets by calculating a life cycles estimate for each. Using statistical methods, the life cycles results are analyzed to determine the effect each of the four basic parameters has on the life of a component with a defect. Understanding the relationship between these four basic parameters and life cycles enables the method to provide an interpolation algorithm for finding the life cycles for any component having a defect.

44 Claims, 8 Drawing Sheets

The 6x4x4x4 matrix – ($t_1$~$t_6$), ($S_1$~$S_4$), ($a_1$~$a_4$) and ($r_1$~$r_4$)

| Temperature(t, °F) | 75 | 250 | 500 | 650 | 750 | 1000 |
|---|---|---|---|---|---|---|
| Stress (S, Ksi) | 50 | 75 | | 100 | | 125 |
| Defect Area (a, in$^2$) | 9e-4 | 3.6e-3 | | 1.44e-2 | | 5.76e-2 |
| Defect Shape(r) | 1 | 4 | | 16 | | 64 |

Fig. 3

DATA SET 1 = ($t_1$, $S_1$, $a_1$, $r_1$)

DATA SET 2 = ($t_1$, $S_1$, $a_1$, $r_2$)

DATA SET 383 = ($t_6$, $S_4$, $a_4$, $r_3$)

DATA SET 384 = ($t_6$, $S_4$, $a_4$, $r_4$)

Fig. 4

METHODS AND SYSTEMS FOR EVALUATING DEFECTS IN METALS

TECHNICAL FIELD

The described technology relates to the evaluation of structural defects in metals, and in particular, to the evaluation of structural defects in IN718 alloy forgings.

BACKGROUND

Nickel alloys demonstrate excellent mechanical properties at high temperatures. As a result, these alloys are often used to make components that will be subjected to high loads and high temperatures in service. IN718, for example, is one particular nickel alloy that is frequently used to make internal components for large land-based gas turbines. Although nickel alloys do demonstrate excellent mechanical properties, defects can occur in nickel alloy forgings during the melting and forging processes due to the chemistry of the alloys. Not all of these defects are unacceptable, however, and conventional fracture mechanics analyses are frequently employed to show that many of these defects can be accepted.

Evaluating a forging defect can prove to be a complicated and time-consuming process using conventional analytical methods. These methods often require considerably more information about the defect than just the basic parameters of defect size, defect location, and defect operating stress and temperature. For example, conventional methods for evaluating defects in IN718 forgings can additionally require other parameters known to those of skill in the fracture mechanics art, such as the offset of the defect from the forging surface, the fracture toughness of the material, the threshold of fracture toughness of the material, and the surface crack distortion factor. Perhaps even more onerous, these methods often require solving esoteric fracture mechanics equations such as the Paris equation for crack growth rate (to obtain the coefficient C and exponent n), and the Walker equation for the stress intensity factor (to obtain the exponents m+ and m−). As will be appreciated by those of skill in the relevant art, an engineering background in fracture mechanics, if not a basic prerequisite, can greatly facilitate using conventional methods to evaluate forging defects.

FIG. 1 is a flow diagram illustrating how a typical forging evaluation using conventional methods might proceed after ultrasonic testing has indicated the presence of a defect in the forging. In block 102, a non-destructive test ("NDT") engineer determines the size and location of the defect and provides this information to a design engineer. The design engineer in block 104 determines the operating stress and temperature at the location on the component to be made from the forging that corresponds to the location of the defect on the forging. The size, location, stress, and temperature information is then provided to a fracture mechanics ("FM") engineer who in block 106 uses this information, along with additional fracture mechanics parameters such as those discussed above, to determine the number of life cycles the finished component would safely survive if made from the forging in question. The resulting number of life cycles is then provided to the design engineer in block 108. One "life cycle" in this context refers to one on/off cycle of the machine in which the finished component is ultimately installed. For example, if the finished component is ultimately installed in a turbine, then one life cycle is equivalent to turning the turbine on and off one time.

In decision block 110, if the design engineer determines that the finished component will survive a sufficient number of life cycles (5000 in this example), then the forging is accepted. If the design engineer determines that the component will not survive a sufficient number of cycles, then in block 112 the design engineer will try to reorient the finished component with respect to the uncut forging in an effort to relocate the defect to a region of lower stress or temperature. If the design engineer is successful in relocating the defect, then the new lower stress and temperature parameters are provided back to the fracture mechanics engineer. In block 114, the fracture mechanics engineer reevaluates the component using the new lower parameters, and provides the new life cycles estimate back to the design engineer in block 116. In decision block 118, if the life cycles requirement is now satisfied by the new life cycles estimate, then the forging is accepted. Otherwise, the forging may be finally rejected.

As the foregoing example illustrates, it can be a lengthy process from the time a defect is initially detected to the time a final decision regarding forging acceptance is made. In addition, the process can require several iterations and the participation of several different specialists, most notably, a fracture mechanics engineer. Accordingly, an accurate and user-friendly method for quickly and simply evaluating forging defects that does not require an expertise in fracture mechanics would be desirable.

BRIEF DESCRIPTION OF THE DRAWINGS

FIG. 3 illustrates a table containing selected index values defining the ranges of four basic defect parameters, in accordance with an embodiment.

FIG. 4 illustrates a list of generated data sets representing all possible combinations of selected index values, in accordance with an embodiment.

DETAILED DESCRIPTION

Figure 1:
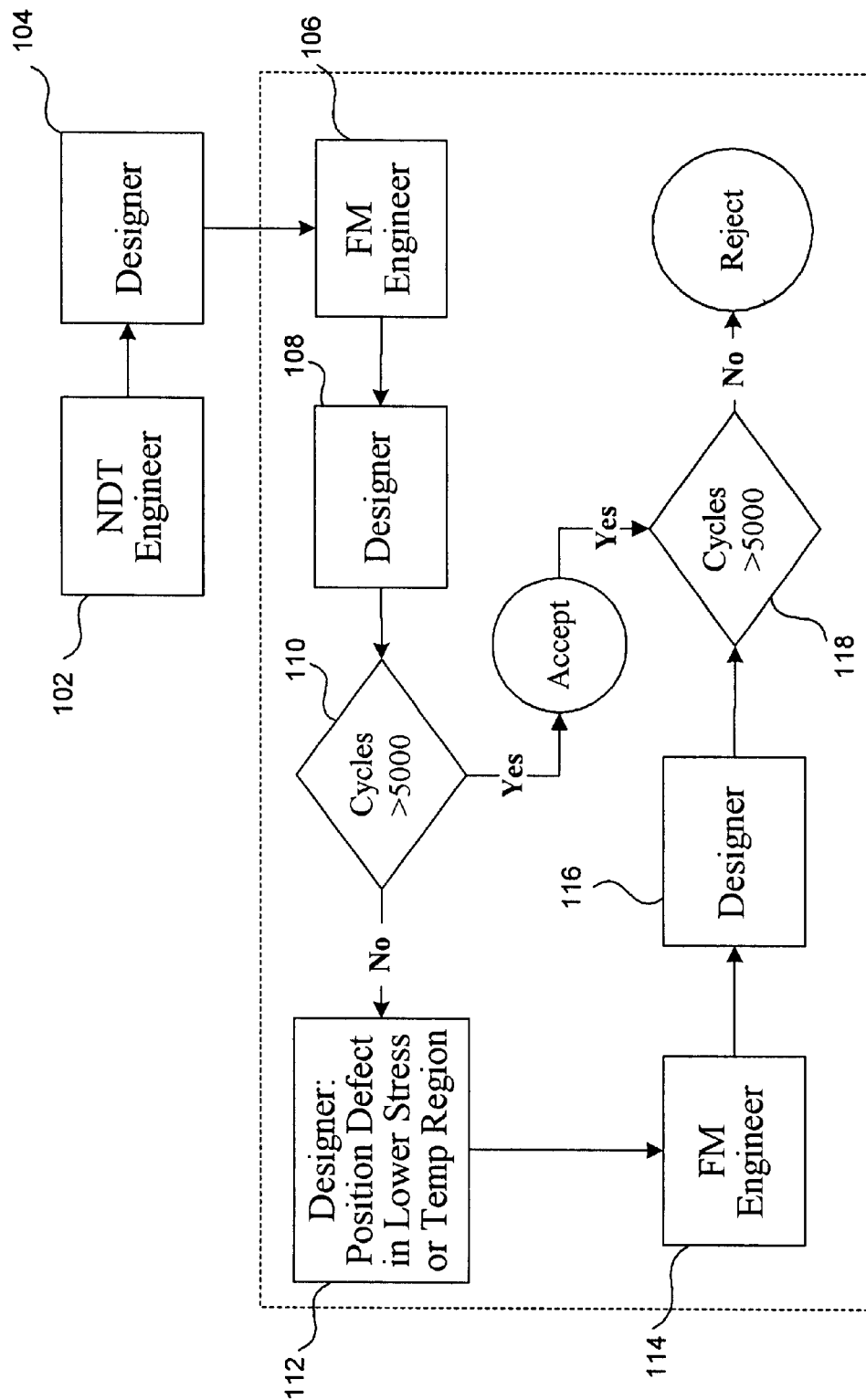
FIG. 1 is a flow diagram illustrating an evaluation process for a forging having a defect, in accordance with conventional methods.

A method and system for evaluating structural defects in metals is provided. In one embodiment, the method provides an accurate and user-friendly routine for evaluating forging defects that does not require specialized skill in fracture mechanics for implementation. Unlike some conventional methods that require calculation of multiple complex fracture mechanics parameters, the method described in the present disclosure recognizes that the acceptability of a given defect is principally determined by only four basic parameters. The more complex fracture mechanics parameters often required by conventional methods either have a minimal effect or can be directly correlated to one or more of the four basic parameters. By requiring only four basic parameters as input, the method allows a user of average technical ability to determine the life cycles of a component having a particular defect.

In one embodiment, the method evaluates defects based on the four basic parameters of temperature, stress, defect area (length×width), and defect shape (length-to-width ratio). Ranges are established for each of these four basic parameters. In one aspect of this embodiment related to forgings for components for large land-based gas turbines, a temperature range of 75° F. to 1,000° F., and a stress range of 50 to 125 KSI, should encompass all of the possible operating conditions. Similarly, an area range from 0.0009 inch$^2$ to 0.0576 inch$^2$, and a shape range from 1 to 64, should encompass all of the foreseeable defect areas and shapes for such forgings. In another aspect of this embodiment, intermediate values within the ranges of the four basic parameters are then selected to create a full series of index values defining each range. For example, intermediate temperature values of 250° F., 500° F., 650° F., and 750° F. within the limits of 75° F. to 1,000° F. can be selected to create the full series of temperature index values of 75° F., 250° F., 500° F., 650° F., 750° F., and 1,000° F. A matrix comprising all possible combinations of the index values for the four basic parameters is then assembled. These combinations are referred to as index value data sets.

Using fracture mechanics equations, the method evaluates these index value data sets. In one embodiment, the method evaluates the data sets by calculating a life cycles estimate for each of the index value data sets previously assembled. In other embodiments, other measures of performance, e.g., strength limit or usable lifetime, can be calculated for the data sets. Using statistical methods, the life cycles results are analyzed to determine the effect each of the four basic parameters of temperature, stress, defect area, and defect shape has on the life cycles estimate of a component with the defect. Understanding the relationship between these four basic parameters and life cycles enables the method to provide an interpolation algorithm for finding the life cycles of any component having a defect defined by a data set that falls anywhere within the ranges of the four basic parameters.

To determine the life cycles of a component having a defect in accordance with the methods described, the four basic parameters of temperature, stress, defect area and defect shape corresponding to the particular defect are first determined. The index values that bracket these defect parameters are then identified, and bracketing index value data sets are generated. The method then uses the interpolation algorithm to interpolate between the known life cycles for the bracketing index value data sets to determine the life cycles corresponding to the particular defect in question. By interpolating between two points where the life cycles are known, the life cycles corresponding to the particular defect can be found. In other embodiments, other measures of performance for the component having the defect can be determined using the methods disclosed. For example, instead of life cycles a strength limit or a usable lifetime can be determined.

In one embodiment of the system, a user can determine the life cycles of a component having a defect by inputting some basic defect information into a computerized display description. For example, the user can input basic information such as the type of forging material, the operating temperature, the operating stress, and the length and width of the defect. In one aspect of this embodiment, by clicking a button on the display description, the method will automatically display for the user the number of life cycles for the component in question.

In another aspect of this embodiment, the number of life cycles for the component in question can be displayed for the user on a computerized display description in three different formats. For example, if the calculated component life is greater than 5,500 cycles, then a green display description can indicate to the user that the component is acceptable. Conversely, if the calculated component life is less than 4,500 cycles, a red display description can indicate to the user that the component is unacceptable. Finally, if the calculated component life is between 4,500 and 5,500 cycles, then a yellow display description can indicate to the user that further evaluation of the forging, perhaps using conventional methods, may be required.

The following description provides specific details and an enabling description for a thorough understanding of several embodiments of the methods and systems disclosed. One skilled in the relevant art, however, will understand that the methods and systems may be practiced without these details. In other instances, well-known structures and functions associated with metallic defect evaluation, such as computer systems and computer-executable instructions for conventional fractures mechanics analyses, have not been shown or described in detail to avoid unnecessarily obscuring the description of the embodiments.

Figure 2:
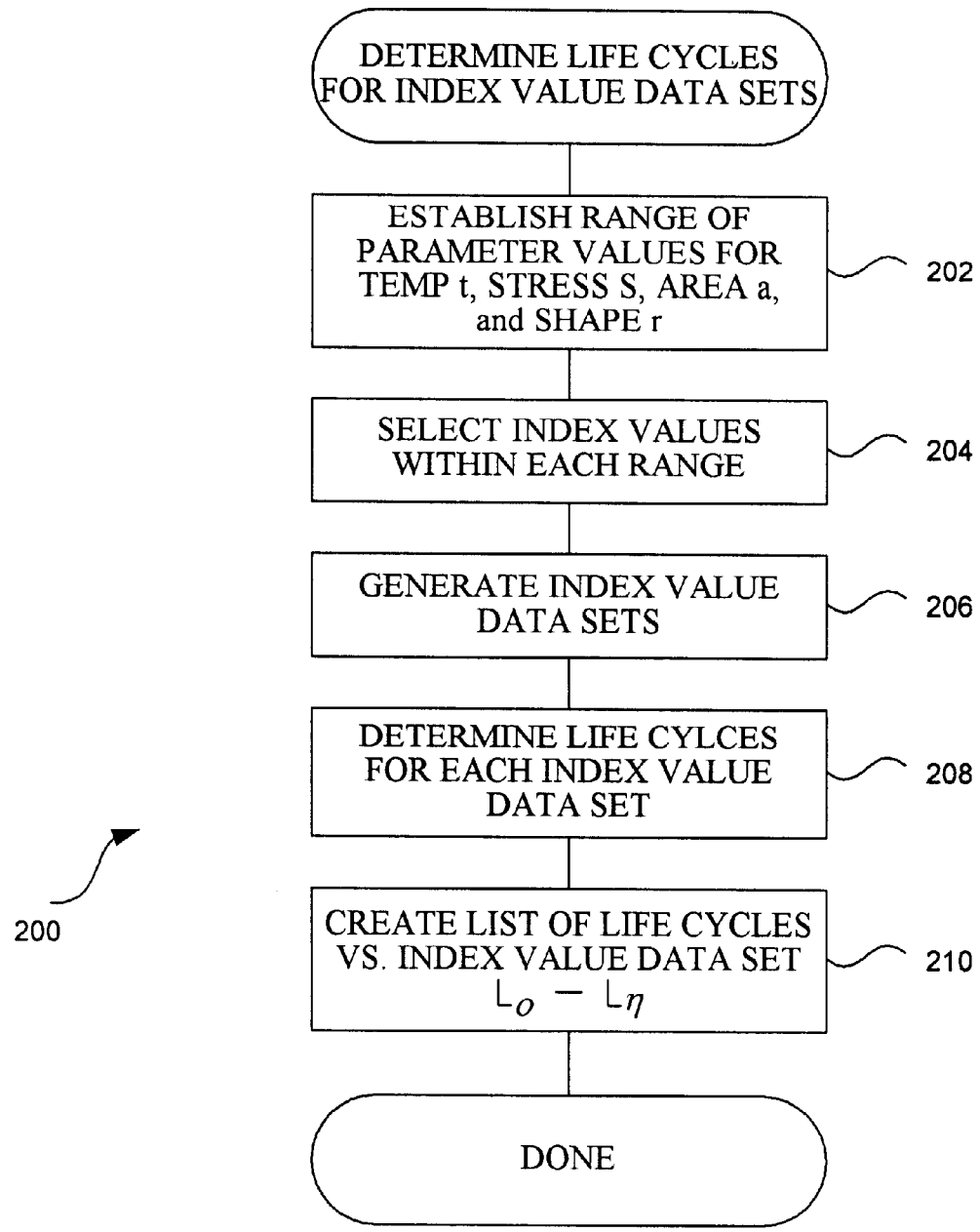
FIG. 2 is flow diagram illustrating a routine for creating a list of life cycles corresponding to generated data sets, in accordance with an embodiment.

FIG. 2 is a flow diagram illustrating a routine 200 for creating a list of life cycles $L_0$–$L_\eta$ corresponding to $\eta+1$ generated data sets, in accordance with an embodiment. Each generated data set contains selected index values for the four basic parameters of temperature, stress, defect area, and defect shape corresponding to a particular defect. The life cycles corresponding to each data set refers to the number of on/off cycles a component made from a forging having the defect could safely survive. In one aspect of this embodiment, the list of life cycles $L_0$–$L_\eta$ is created using fracture mechanics equations. In other embodiments, other methods, such as empirical methods, can be used to create the list of life cycles.

In block 202, the routine 200 begins by establishing operating ranges for each of the four basic parameters of temperature, stress, defect area, and defect shape. In aspects of this embodiment as it pertains to IN718 forgings for turbine components, the possible range of operating temperatures is from 75° F. to 1,000° F., and the possible range of stresses that a defect could experience in service ranges from 50 KSI to 125 KSI. Similarly, the defect area for such forgings can range from 0.0009 inch$^2$ to 0.0576 inch$^2$, and the defect shape can range from 1 to 64. Once the ranges of the four basic parameters have been established, in block 204 intermediate values within these ranges are selected to define a set of index values for each parameter.

FIG. 3 illustrates a table 300 containing a range for each of the four basic defect parameters in accordance with an embodiment. The four basic parameters are shown in a column 302, and index values that define the range of the parameters are shown in a column 304. In this embodiment, the ranges shown in table 300 apply to IN718 forgings as used to make gas turbine components. In other embodiments, other ranges can be established for the four basic parameters depending on the particular application or metal in question. In one aspect of this embodiment, the range of possible temperatures is represented by six index values, and the ranges of stress, defect area, and defect shape are represented by four index values. For example, the index values of the stress parameter as shown in column 304 are: 50, 75, 100, and 125 KSI. In another aspect of this embodiment, the temperature index values can be represented as $t_1$ through $t_6$, the stress index values as $S_1$ through $S_4$, the area index values as $\alpha_1$ through $\alpha_4$, and the defect shape index values as $r_1$ through $r_4$. In other embodiments, more or less index values can be selected depending on the level of refinement desired.

After the range of index values for each of the four basic parameters has been established, the routine 200 in block 206 generates a complete list of data sets corresponding to all the possible combinations of the index values shown in FIG. 3. FIG. 4 illustrates a data set list 400 in accordance with such an embodiment. In this embodiment where there are six index values corresponding to temperature, and four index values corresponding to stress, defect area, and defect shape, the list 400 will accordingly contain 384 different data sets of possible index value combinations. For example, in the list 400 data set 1 contains index values $t_1$, $S_1$, $\alpha_1$, and $r_1$, and data set 384 contains index values $t_6$, $S_4$, $\alpha_4$, and $r_4$. As will be apparent to those of skill in the relevant art, the data sets shown in the list 400 encompass all possible combinations of the index values shown in table 300.

Returning to FIG. 2, in block 208 the routine 200 determines the life cycles for each of the 384 index value data sets listed in FIG. 4. To determine the life cycles in one embodiment, the method starts with the Paris equation as used to calculate a rate-of-change in crack length (or defect length) da, with respect to a rate-of-change in cycles, dN. The Paris equation is shown below as Equation (1):

$$\text{Paris equation } \frac{da}{dN} = C(\Delta K)^n \quad (1)$$

In Equation (1), C and n are constants corresponding to the temperature index value contained in the particular index value data set being evaluated, and K is the stress intensity factor. K can be calculated using Equation (2) below:

$$\text{Stress intensity factor } K = G\sigma\sqrt{\pi\alpha} \quad (2)$$

In Equation (2), (G is a geometric factor which can be calculated, $\sigma$ is the applied stress, and $\alpha$ is the defect length. From Equation (2) it can be seen that:

$$\Delta K = G\Delta\sigma\sqrt{\pi\alpha}, \text{ where } \Delta\sigma = \sigma_{max} - \sigma_{min} \quad (3)$$

The change in the applied stress $\Delta\sigma$ (where $\sigma$ equals the basic stress parameter S in this disclosure), and the defect length $\alpha$, can both be provided by the particular index value data set being evaluated.

Inserting Equation (3) for $\Delta K$ into Equation (1) yields Equation (4) below:

$$\frac{da}{dN} = C\left(G\Delta\sigma\sqrt{\pi a}\right)^n \quad (4)$$
$$= CG^n \Delta\sigma^n \pi^{n/2} a^{n/2}$$
$$\propto \Delta\sigma^n a^{n/2}$$

Integrating $$\frac{da}{dN}$$

in Equation (4) and rearranging the terms results in Eeuation (5) below for the life cycles N corresponding to a given index value data set:

$$\text{life cycles } N = \frac{a}{\int CG^n \Delta\sigma^n \pi^{n/2} a^{n/2}} \quad (5)$$

As will be apparent to those of skill in the relevant art, the values of $\alpha$, $\Delta\sigma$, C, and n in Equation (5) are provided by the particular data set being evaluated, and the Geometric factor G can be determined based on the defect and component geometry.

Evaluation of Equation (5) above for each of the 384 index value data sets shown in the list 400 of FIG. 4 will produce a life cycle value corresponding to each data set. In block 210 of the routine 200 of FIG. 2, these life cycles can be represented as $L_n$, where n ranges from zero to 383. Accordingly, $L_0$ corresponds to data set 1, $L_1$ corresponds to data set 2, and so on up to $L_{383}$ which corresponds to data set 384.

The method now has at its disposal calculated life cycle values $L_n$ corresponding to every possible combination of temperature, stress, defect area, and defect shape index values. However, the basic parameters of temperature, stress, defect area, and defect shape for a particular defect will, in all probability, not coincide exactly with any of the index values. Thus, a method is needed for finding the life cycles of a defect whose basic parameters do not coincide with the index values.

Figure 5:
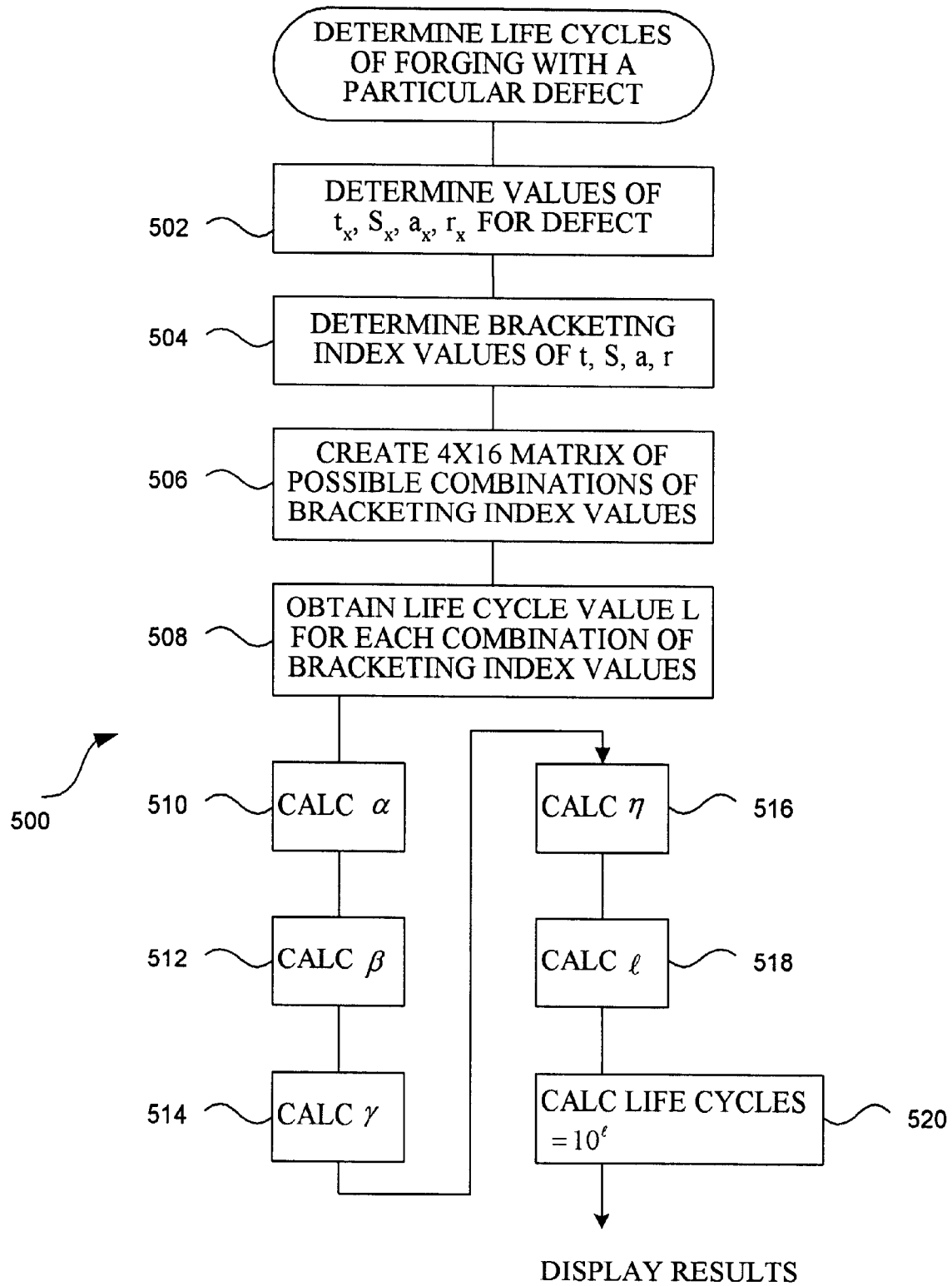
FIG. 5 illustrates a routine for determining the life cycles of a component made from a forging having a defect, in accordance with an embodiment.

FIG. 5 illustrates a routine 500 for determining the life cycles of a component having a defect defined by any given set of basic parameters, in accordance with an embodiment. In block 502, the routine 500 begins by determining the values of the four basic parameters of temperature ($t_x$), stress ($S_x$), defect area ($\alpha_x$), and defect shape ($r_x$) for the particular defect in question. This set of defect parameters can be obtained by a design engineer using known methods, and should not require the expertise of a fracture mechanics engineer. The values of the four basic parameters of temperature, stress, defect area, and defect shape for the defect in question will fall somewhere between the index values selected for the four basic parameters. Thus, the data set of ($t_x$, $S_x$, $\alpha_x$, and $r_x$) will probably not coincide exactly with any of the index value data sets previously assembled and shown in FIG. 4.

In block 504, the routine 500 determines bracketing index values of the parameters t, S, $\alpha$, and r that bracket the parameters $t_x$, $S_x$, $\alpha_x$, and $r_x$, corresponding to the defect in question. The bracketing values are defined as the two index values of a given parameter which bracket the actual parameter value corresponding to the defect. For example, referring to table 300 in FIG. 3, if the temperature parameter corresponding to a defect in question is 300° F., then the bracketing values of t would be $t_2$ of 250° F. and $t_3$ of 500° F. Similarly, if the stress parameter of the defect was 110 KSI, then the bracketing values of S would be $S_3$ of 100 KSI and $S_4$ of 125 KSI. The results of the foregoing exercise will be four pairs of bracketing index values; one pair for each of the four basic parameters.

Figure 6:
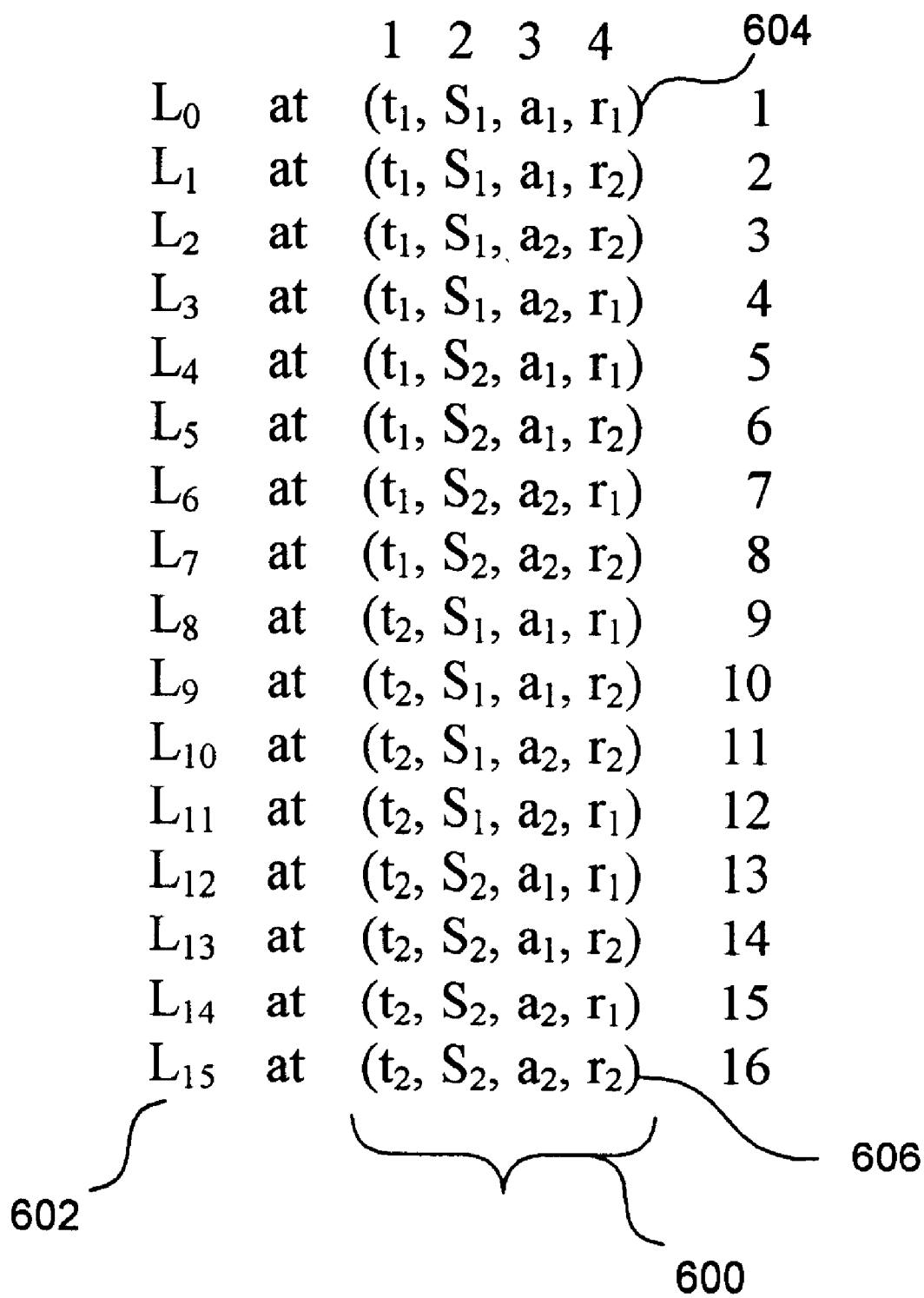
FIG. 6 illustrates a list of bracketing index value data sets in accordance with an embodiment.

In block 506, the routine 500 creates a 4×16 matrix encompassing all possible combinations of the bracketing index values determined in block 504. As an example, consider a defect having the basic parameters of $t_x$, $S_x$, $\alpha_x$, and $r_x$ that fall within the intervals of bracketing index values $(t_1, t_2)$, $(S_1, S_2)$, $(\alpha_1, \alpha_2)$, and $(r_1, r_2)$. A 4×16 matrix can be created that encompasses all possible combinations of these bracketing index values. FIG. 6 illustrates such a 4×16 matrix 600 in accordance with this embodiment.

In block 508 of the routine 500, once the matrix 600 of FIG. 6 has been created, the list of life cycles created by the routine 200 of FIG. 2 is accessed to provide a life cycle 602 corresponding to each combination of bracketing index values. The life cycles 602 can be represented by $L_0$ for a first index value data set 604 and so on up to $L_{15}$ for a 16th index value data set 606. At this point in the method, the life cycles $L_0$ through $L_{15}$ for the index values which bracket the basic parameters of the defect in question are known and listed in FIG. 6. To find the life cycles corresponding to the defect in question, the method interpolates between these known life cycles.

The relationships between each of the four basic defect parameters and life cycles have been determined for use in the methods described herein using statistical analysis in accordance with an embodiment. In one aspect of this embodiment, the log of the life cycles is determined to have a linear relationship to the stress parameter. In another aspect of this embodiment, the log of the life cycles is determined to have a linear relationship to the log of the temperature, area, and shape parameters. From these relationships, a suitable interpolation algorithm has been developed. Accordingly, if the life cycles are known for index value data sets which bracket the parameters of the defect in question, then the life cycles corresponding to the defect in question can be determined using the interpolation algorithm of this embodiment.

Interpolation between the bracketing index value data sets to determine the life cycles corresponding to a particular defect requires determining an $\alpha$ interpolation factor for the temperature, a $\beta$ interpolation factor for the stress, a $\gamma$ interpolation factor for the area of the defect, and an $\eta$ interpolation factor for the shape of the defect. In block 510 of the routine 500 shown in FIG. 5, the $\alpha$ interpolation factor is calculated using Equation (6) below:

$$\alpha = \frac{\log_{10}(t/t_1)}{\log_{10}(t_2/t_1)} \quad (6)$$

In Equation (6), t is equal to the temperature parameter for the particular defect in question, and $t_1$ and $t_2$ are equal to the index values which bracket the temperature parameter t. In this example, the temperature parameter t for the defect in question happens to fall between the bracketing index values of $t_1$ and $t_2$. In other embodiments, the temperature parameter can fall between other bracketing index values.

In block 512 of the routine 500, interpolation in accordance with the present method also requires the calculation of the $\beta$ interpolation factor in accordance with Equation (9) below. Calculation of $\beta$ using Equation (9), however, first requires calculating a $\beta 0$ and a $\beta 1$ in accordance with Equations (7) and (8) below:

$$\beta_0 = \frac{S - S_1}{S_2 - S_1} \quad (7)$$

$$\beta_1 = \begin{cases} \beta_0 & |S - 62| \geq 10 \\ \dfrac{1.15\beta_0}{1 + 0.15\beta_0} & |S - 62| < 10 \end{cases} \quad (8)$$

In Equations (7) and (8), S is equal to the stress parameter for the particular defect in question, and $S_1$ and $S_2$ are equal to the index values which bracket the stress parameter S. Once $\beta 0$ and $\beta 1$ have been calculated using Equations (7) and (8), Equation (9) can be used to calculate the value of $\beta$:

$$\beta = \begin{cases} \beta_1 & |S - 87| \geq 10 \\ \dfrac{1.1\beta_1}{1 + 0.1\beta_1} & |S - 87| < 10 \end{cases} \quad (9)$$

In block 514 of the routine 500, the $\gamma$ interpolation factor is calculated in accordance with Equation (10) below:

$$\gamma = \frac{\log_{10}(a/a_1)}{\log_{10}(a_2/a_1)} \quad (10)$$

In Equation (10), $\alpha$ is equal to the area parameter for the particular defect in question, and $\alpha_1$ and $\alpha_2$ are equal to the index values which bracket the area parameter $\alpha$.

In block 516 of the routine 500, the $\eta$ interpolation factor is calculated in accordance with Equation (11) below:

$$\eta = \frac{r - r_1}{r_2 - r_1} \quad (11)$$

In Equation (11) r is equivalent to the shape parameter for the particular defect in question, and $r_1$ and $r_2$ are equivalent to the index values which bracket the shape parameter r.

After the interpolation factors of $\alpha$, $\beta$, $\gamma$, and $\eta$ have been determined for the particular defect in question, in block 518 of the routine 500 the method calculates a life cycles exponent l using Equation (12) below:

$$\begin{aligned}
l = &(\log_{10} L_0) \times [(1-\alpha)(1-\beta)(1-\gamma)(1-\eta)] + \\
&(\log_{10} L_1) \times [(1-\alpha)(1-\beta)(1-\gamma)\cdot\eta] + \\
&(\log_{10} L_2) \times [(1-\alpha)(1-\beta)\gamma\cdot\eta] + \\
&(\log_{10} L_3) \times [(1-\alpha)(1-\beta)\gamma\cdot(1-\eta)] + \\
&(\log_{10} L_4) \times [(1-\alpha)\cdot\beta\cdot(1-\gamma)(1-\eta)] + \\
&(\log_{10} L_5) \times [(1-\alpha)\cdot\beta(1-\gamma)\cdot\eta] + \\
&(\log_{10} L_6) \times [(1-\alpha)\cdot\beta\cdot\gamma\cdot(1-\eta)] + \\
&(\log_{10} L_7) \times [(1-\alpha)\cdot\beta\cdot\gamma\cdot\eta] + \\
&(\log_{10} L_8) \times [\alpha\cdot(1-\beta)(1-\gamma)(1-\eta)] + \\
&(\log_{10} L_9) \times [\alpha\cdot(1-\beta)(1-\gamma)\cdot\eta] + \\
&(\log_{10} L_{10}) \times [\alpha\cdot(1-\beta)\cdot\gamma\cdot\eta] + \\
&(\log_{10} L_{11}) \times [\alpha\cdot(1-\beta)\cdot\gamma\cdot(1-\eta)] + \\
&(\log_{10} L_{12}) \times [\alpha\cdot\beta\cdot(1-\gamma)(1-\eta)] + \\
&(\log_{10} L_{13}) \times [\alpha\cdot\beta\cdot(1-\gamma)\eta] + \\
&(\log_{10} L_{14}) \times [\alpha\cdot\beta\cdot\gamma\cdot(1-\eta)] + \\
&(\log_{10} L_{15}) \times [\alpha\cdot\beta\cdot\gamma\cdot\eta]
\end{aligned} \quad (12)$$

In addition to using the values of $\alpha$, $\beta$, $\gamma$, and $\eta$, Equation (12) also requires the 16 life cycle values $L_0$ through $L_{15}$ shown in column 602 of FIG. 6 which correspond to the bracketing index value data sets for the defect. In block 520, once the life cycles exponent l has been determined using Equation (12) above, the life cycles for a component having the particular defect in question is determined in an embodiment using Equation (13) below:

$$\text{Life cycles} = 10^l \qquad (13)$$

Although the methods described above for finding life cycles have been explained with reference to interpolation, those of skill in the art will recognize that the methods can also be practiced in other embodiments without the use of interpolation. For example, if the number of index values for each parameter is substantially increased beyond the four or six used above, then the life cycles of a component can be estimated by simply using the life cycles for the index value data set that best matches the data set corresponding to the component. For another example, if the data set corresponding to a component having a defect happens to fall outside of the ranges of the four basic parameters, then extrapolation, rather than interpolation, can be used to find the life cycles of the component in accordance with the methods described above. These and other embodiments of the methods disclosed above are possible without departing from the scope of the present disclosure.

In other embodiments of the methods and systems described, display descriptions can be provided for user interfaces with the routines shown above. For example, various display descriptions can be created for a user to input the basic parameters of $t_x$, $S_x$, $\alpha_x$, and $r_x$ into the routine 500 as called for in block 502. In another embodiment, a display description can be provided for indicating to the user the results of block 520 in terms of the life cycle value.

Figure 7:
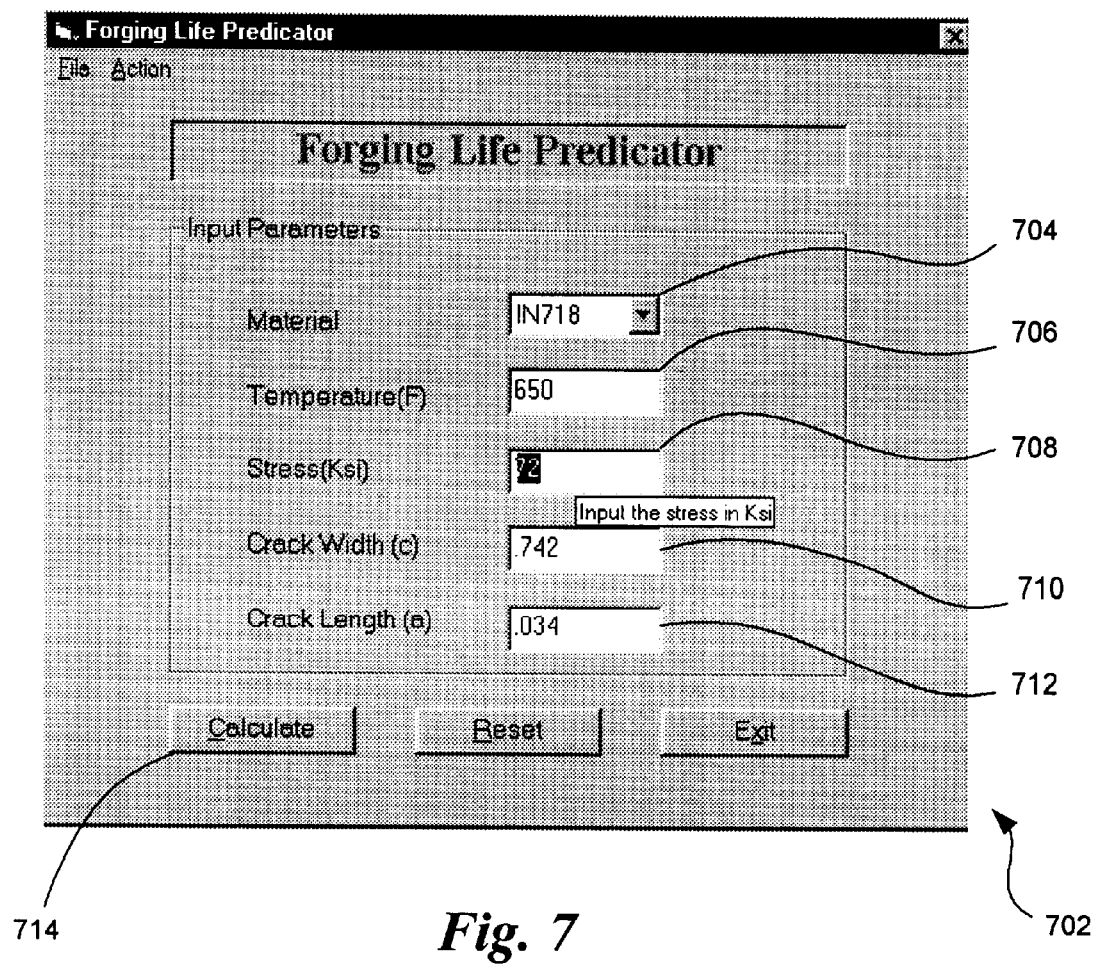
FIG. 7 illustrates a display description for inputting basic defect parameters into a routine for determining the life cycles of a component having the defect, in accordance with an embodiment.

FIG. 7 illustrates a display description 702 that can be used to input the four basic defect parameters into the routine 500 of FIG. 5 in one embodiment. Importantly, the display description 702 contains a material field 704 that includes a pull down menu for selecting the applicable material type. For example, in this particular embodiment the forging material in question is IN718 nickel alloy. The material type can dictate the values of the various material factors used in the method. In other embodiments, the method can be applied to other materials using other appropriate material factors. The display description 702 also includes a temperature parameter field 706 for entering t, a stress parameter field 708 for entering S, a crack width field 710, and a crack length field 712. The defect area parameter α can be determined by multiplying the crack width by the crack length. Similarly, the defect shape parameter r can be determined by dividing the crack width by the crack length. By clicking on a calculate button 714, the user can automatically request a display description indicating the acceptability of the forging.

Figure 8A:
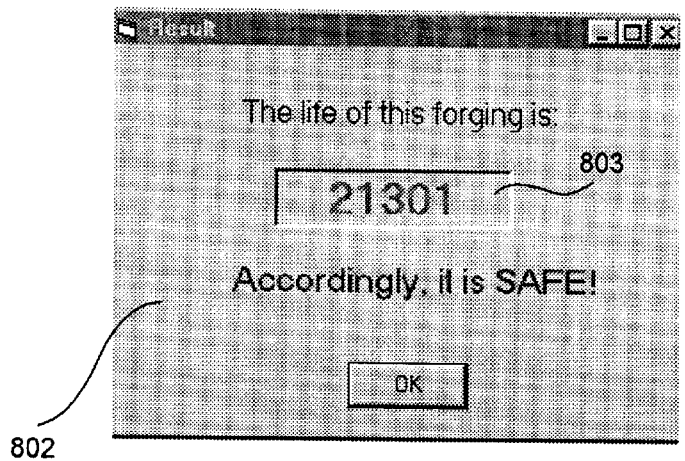
FIGS. 8A–8C collectively illustrate alternative display descriptions for indicating the acceptability of a forging having a particular defect, in accordance with an embodiment.
Figure 8B:
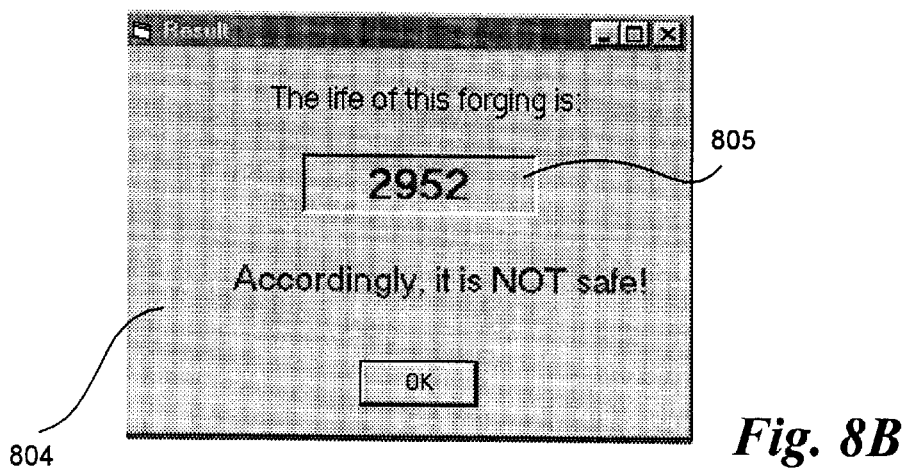
Figure 8C:
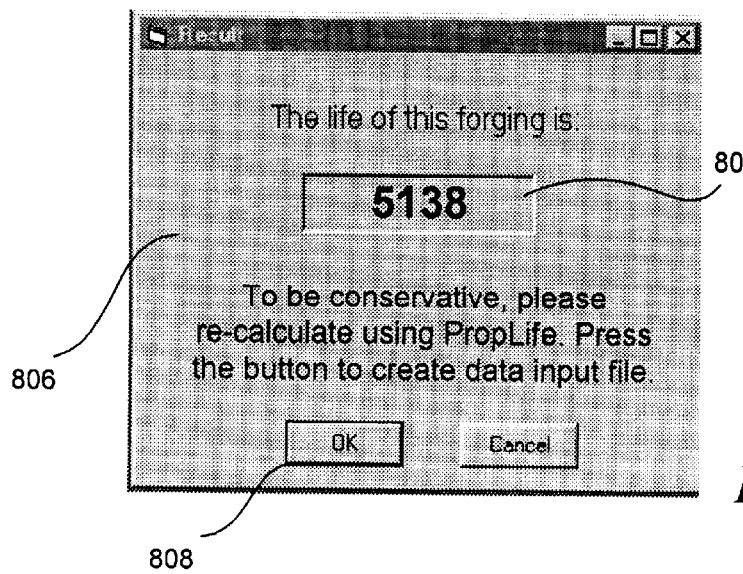

FIGS. 8A through 8C collectively illustrate display descriptions that can be used to indicate the acceptability of a forging with a particular defect in accordance with an embodiment. In one aspect of this embodiment, a component made from an IN718 forging should be able to safely survive at least 5,000 on/off cycles in order to be considered safe for use. If a 10 percent tolerance factor is used, then 5,500 cycles would be needed for an acceptable component, and anything less than 4,500 cycles would be considered unacceptable. In another aspect of this embodiment, life cycles between 4,500 and 5,500 could be considered questionable and require further analysis before a final determination is made.

In a display description 802 of FIG. 8A, an example value of 21,301 in a green life cycle field 803 indicates an acceptable component, and hence an acceptable forging. A display description 804 in FIG. 8B in contrast illustrates an example value of 2,952 in a red life cycle field 805, indicating that the component is not acceptable. A display description 806 as shown in FIG. 8C can be used when the component may be acceptable. If the life cycles fall between 4,500 and 5,500 cycles, a more detailed analysis may be required to make a conclusive determination of the forging's acceptability. A yellow life cycle field 807 indicates the value of 5,138 cycles requires further evaluation. A recalculate button 808 provides the user with an option of creating a data input file to be used for subsequent more comprehensive analysis of the defect.

Figure 9:
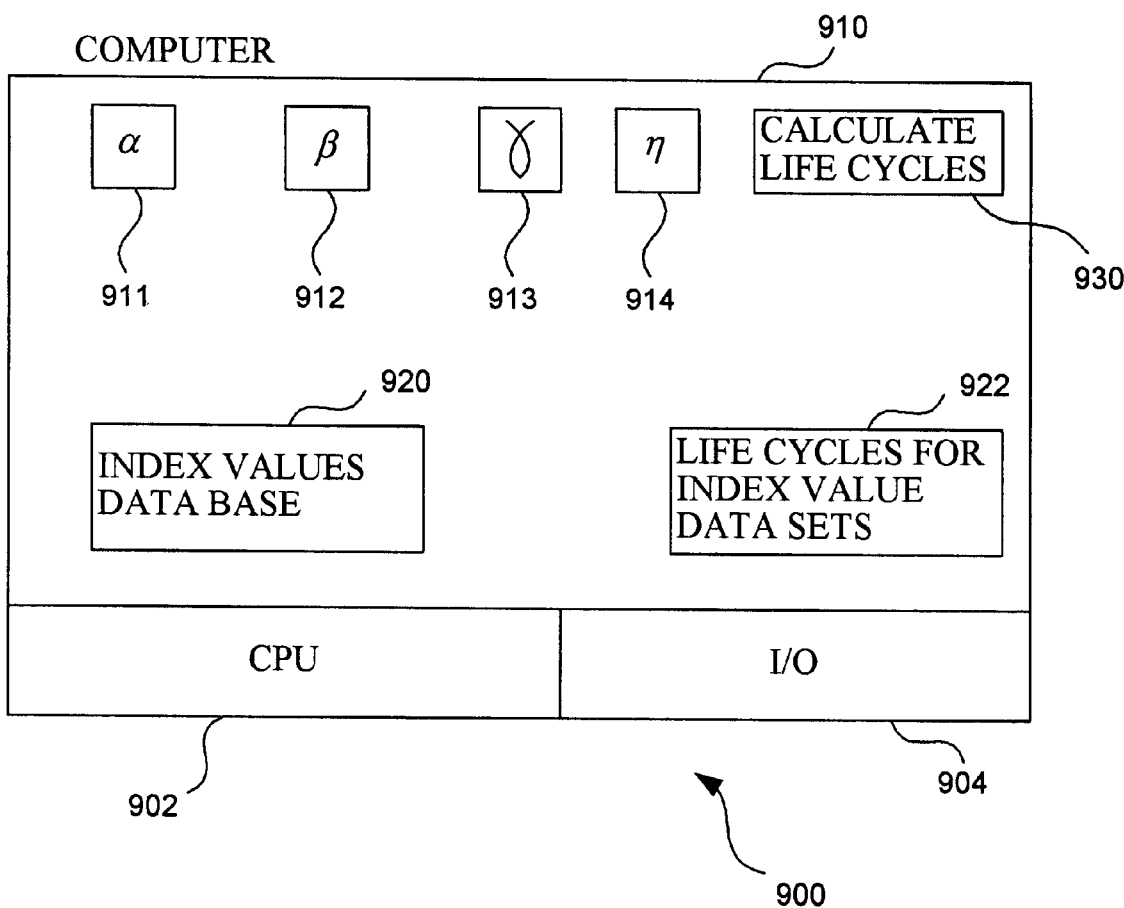
FIG. 9 is a block diagram of a computer system for determining the life cycles of a component having a defect, in accordance with an embodiment.

FIG. 9 is a block diagram of a computer system 900 for determining the life cycles of a component having a defect in accordance with the methods described above. The computer system 900 includes a central processing unit 902, input/output devices 904, and a memory 910. The central processing unit 902 can include circuitry for performing computer functions, such as executing software to perform desired calculations and tasks. The input/output devices 904 can include automatic input devices such as a computer-readable media drive, or manual input devices such as a keypad or mouse, for inputting data into the central processing unit 902. The input/output devices 904 can also include output devices coupled to the central processing unit 902, such as a printer or a display screen, for displaying or otherwise outputting data.

The computer memory 902 can include storage media containing computer-executable instructions for performing the various routines described above. For example, the memory 910 can include an α interpolation factor component 911, a β interpolation factor component 912, a γ interpolation factor component 913, and an η interpolation factor component 914. The a component 911, β component 912, γ component 913, and η component 914 can include computer-executable instructions for determining α, β, γ, and η in accordance with Equations (6)–(11) above. Similarly, a life cycles calculation component 930 can contain computer-executable instructions for calculating life cycles in accordance with Equations (12) and (13) above. An index value database 920 can be used to store the selected index values for the basic parameters, and a life cycles database 922 can accordingly be used to store the life cycles corresponding to the index value data sets.

Those of skill in the art will understand that although the foregoing discussion has referred to IN718 forgings for the purposes of illustration, the methods provided herein are equally applicable to other metallic materials. Those of skill in the art will also appreciate that one advantage of using the methods and systems described herein is the relative ease with which a defect can be evaluated. Instead of requiring the expertise of a fracture mechanics engineer, the present method can be used buy one of average technical ability once a non-destructive test engineer has identified a defect. In addition, use of the methods provided herein only require the four basic parameters of temperature, stress, defect area and defect shape. Evaluation of complex fracture mechanics equations is not required to either evaluate the defect or interpret the results of the evaluation.

In general, unless specifically set forth to the contrary herein, the claims should not be construed as limited to the specific embodiments disclosed in the specification and claims, but should instead be construed to include all methods and systems for evaluating defects in metals under the teachings disclosed herein. For example, although 5,000 cycles has been referred to as the requirement for IN718 forgings, it will be appreciated that other limiting ranges can be established for other types of metals and for other purposes. Further, although the number of index values chosen for the four basic parameters numbered between 4 and 6 in the present disclosure, it will be readily appreciated by those of skill in the relevant art that more index values could be selected to define the parameter ranges where further refinement is desired. Conversely, less could be selected where accuracy can be sufficient. Similarly, other basic parameters in addition to the four disclosed herein can be selected when deemed relevant without departing from the scope or intent of the present disclosure. Accordingly, the present disclosure is not limited except as by the appended claims.

We claim:

1. A method in a computer system for estimating a number of life cycles a component having a defect can experience before failure, the component being subjected to an operating temperature and an operating stress during operation, the defect being definable by a defect dimension, the method comprising:

providing a temperature range comprising a plurality of temperature index values, a stress range comprising a plurality of stress index values, and a dimension range comprising a plurality of dimension index values;

providing a plurality of index value data sets, wherein each index value data set comprises one temperature index value, one stress index value, and one dimension index value;

determining life cycles estimates for a plurality of the index value data sets;

selecting two temperature index values that bracket the operating temperature, two stress index values that bracket the operating stress, and two dimension index values that bracket the defect dimension;

determining a temperature interpolation factor based on the two bracketing temperature index values and the operating temperature, a stress interpolation factor based on the two bracketing stress index values and the operating stress, and a dimension interpolation factor based on the two bracketing dimension index values and the defect dimension; and determining a life cycles estimate for the component having the defect based on the temperature interpolation factor, the stress interpolation factor, the dimension interpolation factor, and a plurality of the index value data set life cycles.

2. A method in a computer system for estimating a number of life cycles a component having a defect can experience before failure, the component being subjected to an operating temperature and an operating stress during operation, the defect being definable by a defect dimension, the method comprising:

providing a first parameter data set comprising a first temperature parameter, a first stress parameter, and a first dimension parameter;

providing a second parameter data set comprising a second temperature parameter, a second stress parameter, and a second dimension parameter;

providing a third parameter data set comprising a third temperature parameter, a third stress parameter, and a third dimension parameter, wherein the third temperature parameter is between the first and second temperature parameters, the third stress parameter is between the first and second stress parameters, and the third dimension parameter is between the first and second dimension parameters;

determining a first number of life cycles based on the first parameter data set;

determining a second number of life cycles based on the second parameter data set; and determining a third number of life cycles based on the first and second numbers of life cycles.

3. The method of claim 2 wherein the third number of life cycles is determined based on the first number of life cycles, the second number of life cycles, and the relationship between the third parameter data set and the first and second parameter data sets.

4. The method of claim 2 wherein the third number of life cycles is determined by interpolation.

5. The method of claim 2 wherein the third number of life cycles is determined by extrapolation.

6. A method in a computer system for evaluating a metallic component having a defect, the method comprising:

providing two or more index value data sets, wherein each index value data set comprises a temperature index value, a stress index value, and a dimension index value;

evaluating the two or more index value data sets to determine a measure of performance for each of the two or more index value data sets; and interpolating between the measures of performance for the two or more index value data sets to determine a measure of performance for the metallic component having the defect.

7. The method of claim 6 wherein the measures of performance determined for the two or more index value data sets are numbers of life cycles, and the measure of performance determined for the metallic component is a number of life cycles.

8. The method of claim 6 wherein the measures of performance determined for the two or more index value data sets are strength limits, and the measure of performance determined for the metallic component is a strength limit.

9. The method of claim 6 wherein the metallic component is an IN718 nickel alloy component.

10. The method of claim 6 wherein interpolating between the measures of performance includes calculating a logarithm of one of the measures of performance of the index value data sets.

11. The method of claim 6 further comprising:

providing a display description of the measure of performance for the metallic component having the defect, the display description comprising:

a green colored display portion if the measure of performance for the metallic component is acceptable;

a red colored display portion if the measure of performance for the metallic component is unacceptable; and a yellow colored display portion if the measure of performance for the metallic component is questionable.

12. The method of claim 6 further comprising:

receiving a defect data set, wherein the defect data set comprises a temperature value, a stress value, and a dimension value; and wherein interpolating between the measures of performance includes evaluating the relationship between the defect data set and one or more of the index value data sets.

13. The method of claim 12 wherein the dimension value in the defect data set is an area value.

14. The method of claim 12 wherein the dimension value in the defect data set is a shape value.

15. The method of claim 14 wherein the shape value is a length-to-width ratio.

16. A method in a computer system for evaluating a metallic component having a defect, the method consisting essentially of:
   providing a temperature parameter, a stress parameter, an area parameter and a shape parameter corresponding to the defect; and
   calculating a measure of performance for the component based on the temperature, stress, area and shape parameters.

17. The method of claim 16 wherein the measure of performance is a number of life cycles.

18. The method of claim 16 wherein the measure of performance is a strength limit.

19. The method of claim 16 wherein the metallic component is an IN718 nickel alloy component.

20. The method of claim 16 wherein the shape parameter is a ratio of the length of the defect to the width of the defect.

21. A method for estimating a number of life cycles a component having a defect can experience before failure, the component being subjected to an operating temperature and an operating stress during operation, the defect being definable by a defect dimension, the method comprising:
   providing a first life cycles estimate corresponding to a first parameter data set;
   providing a second life cycles estimate corresponding to a second parameter data set;
   providing a defect parameter data set; and
   determining a defect life cycles estimate based on the first and second life cycles estimates and the defect parameter data set.

22. The method of claim 21 wherein:
   the first parameter data set comprises a first temperature parameter, a first stress parameter, or a first dimension parameter; and
   the second parameter data set comprises a second temperature parameter, a second stress parameter, or a second dimension parameter.

23. The method of claim 21 wherein:
   the first parameter data set comprises a first temperature parameter, a first stress parameter, or a first dimension parameter;
   the second parameter data set comprises a second temperature parameter, a second stress parameter, or a second dimension parameter; and
   the defect parameter data set comprises a defect temperature parameter, a defect stress parameter, or a defect dimension parameter, wherein the defect temperature parameter is between the first and second temperature parameters, the defect stress parameter is between the first and second stress parameters, and the defect dimension parameter is between the first and second dimension parameters.

24. The method of claim 23 wherein the defect dimension parameter is an area parameter.

25. The method of claim 23 wherein the defect dimension parameter is a shape parameter.

26. The method of claim 21 wherein:
   the first parameter data set comprises a first temperature parameter, a first stress parameter, and a first dimension parameter;
   the second parameter data set comprises a second temperature parameter, a second stress parameter, and a second dimension parameter; and
   the defect parameter data set comprises a defect temperature parameter, a defect stress parameter, and a defect dimension parameter, wherein the defect temperature parameter is between the first and second temperature parameters, the defect stress parameter is between the first and second stress parameters, and the defect dimension parameter is between the first and second dimension parameters.

27. The method of claim 21 wherein the component is an IN718 nickel alloy component.

28. The method of claim 21 wherein determining the defect life cycles estimate includes interpolating between the first and second life cycles estimates.

29. The method of claim 28 wherein interpolating between the first and second life cycles estimates includes calculating a logarithm of one of the life cycles estimates.

30. The method of claim 21 wherein determining the defect life cycles estimate includes logarithmically interpolating between the first and second life cycles estimates.

31. The method of claim 21 wherein:
   the first parameter data set comprises a first temperature parameter and a first stress parameter; and
   the second parameter data set comprises a second temperature parameter and a second stress parameter.

32. The method of claim 31 wherein the defect parameter data set comprises a defect temperature parameter and a defect stress parameter, and wherein the defect temperature parameter is between the first and second temperature parameters, and the defect stress parameter is between the first and second stress parameters.

33. The method of claim 21 wherein:
   the first parameter data set comprises a first temperature parameter and a first dimension parameter; and
   the second parameter data set comprises a second temperature parameter and a second dimension parameter.

34. The method of claim 33 wherein the defect parameter data set comprises a defect temperature parameter and a defect dimension parameter, and wherein the defect temperature parameter is between the first and second temperature parameters, and the defect dimension parameter is between the first and second dimension parameters.

35. The method of claim 21 wherein:
   the first parameter data set comprises a first stress parameter and a first dimension parameter; and
   the second parameter data set comprises a second stress parameter and a second dimension parameter.

36. The method of claim 35 wherein the defect parameter data set comprises a defect stress parameter and a defect dimension parameter, and wherein the defect stress parameter is between the first and second stress parameters, and the defect dimension parameter is between the first and second dimension parameters.

37. A display description for evaluating a metallic component having a defect, the defect being definable by a first defect dimension and a second defect dimension, the display description consisting essentially of:
   a material input portion;
   a temperature input portion;
   a stress input portion;
   a first defect dimension input portion; and
   a second defect dimension input portion.

38. A computer system for evaluating a metallic component having a defect, the computer system comprising:
   one or more interpolation factor components containing computer-executable instructions for determining one or more interpolation factors;

a life cycles component containing computer-executable instructions for calculating a number of life cycles for the metallic component using one or more of the interpolation factors;

a central processing unit for executing the computer-executable instructions for determining the one or more interpolation factors or the life cycles of the metallic component; and an output device for displaying the life cycles of the metallic component.

39. The computer system of claim 38 wherein the one or more interpolation factor components comprise:

a temperature interpolation component containing computer-executable instructions for determining a temperature interpolation factor;

a stress interpolation component containing computer-executable instructions for determining a stress interpolation factor;

an area interpolation component containing computer-executable instructions for determining an area interpolation factor, and a shape interpolation component containing computer-executable instructions for determining a shape interpolation factor.

40. The computer system of claim 38 wherein the life cycles component contains computer-executable instructions for calculating the number life cycles for the metallic component using logarithmic interpolation.

41. A computer system for estimating a number of life cycles a component having a defect can experience before failure, the component being subjected to an operating temperature and an operating stress during operation, the defect being definable by a defect dimension, the computer system comprising:

means for providing a first parameter data set;

means for providing a second parameter data set;

means for providing a third parameter data set corresponding to the component having the defect;

means for determining a first life cycles estimate based on the first parameter data set;

means for determining a second life cycles estimate based on the second parameter data set; and means for determining a third life cycles estimate corresponding to the component having the defect, the third life cycles estimate being based on the first life cycles estimate, the second life cycles estimate, and the third parameter data set.

42. The computer system of claim 41 wherein:

the first parameter data set comprises a first temperature parameter, a first stress parameter, and a first dimension parameter;

the second parameter data set comprises a second temperature parameter, a second stress parameter, and a second dimension parameter; and the third parameter data set comprises a third temperature parameter, a third stress parameter, and a third dimension parameter, wherein the third temperature parameter is between the first and second temperature parameters, the third stress parameter is between the first and second stress parameters, and the third dimension parameter is between the first and second dimension parameters.

43. A computer-readable medium whose contents cause a computer system to estimate a number of life cycles a component having a defect can experience before failure, the component being subjected to an operating temperature and an operating stress during operation, the defect being definable by a defect dimension, the number of life cycles being estimated by a method comprising:

providing a first life cycles estimate corresponding to a first parameter data set;

providing a second life cycles estimate corresponding to a second parameter data set;

providing a defect parameter data set corresponding to the defect; and determining a defect life cycles estimate based on the first and second life cycles estimates and the defect parameter data set.

44. The computer-readable medium of claim 43 wherein:

the first parameter data set comprises a first temperature parameter, a first stress parameter, and a first dimension parameter;

the second parameter data set comprises a second temperature parameter, a second stress parameter, and a second dimension parameter; and the defect parameter data set comprises the operating temperature, the operating stress, and the defect dimension, and wherein the operating temperature is between the first and second temperature parameters, the operating stress is between the first and second stress parameters, and the defect dimension is between the first and second dimension parameters.

* * * * *